United States Patent [19]
Carli et al.

[11] Patent Number: 5,275,824
[45] Date of Patent: Jan. 4, 1994

[54] THERAPEUTIC COMPOSITIONS WITH CONTROLLED RELEASE OF MEDICAMENTS SUPPORTED ON CROSSLINKED POLYMERS AND COATED WITH POLYMER FILMS, AND THEIR PREPARATION PROCESS

[75] Inventors: Fabio Carli, Trieste; Italo Colombo, Inzago; Leonardo Rabaglia, Parma, all of Italy

[73] Assignee: Vectorpharma International spa, Trieste, Italy

[21] Appl. No.: 620,651

[22] Filed: Dec. 3, 1990

[30] Foreign Application Priority Data

Mar. 6, 1990 [IT] Italy ............................. 19571 A/90

[51] Int. Cl.⁵ ............................................. A61K 9/16
[52] U.S. Cl. ....................................... 424/490; 424/469; 424/486; 424/487; 424/489; 424/497; 514/58

[58] Field of Search ............. 424/469, 489, 490, 501, 424/497, 486, 487; 514/58

[56] References Cited

U.S. PATENT DOCUMENTS 4,973,469  11/1990  Mulligan et al. ............... 424/469 X

*Primary Examiner*—Thurman K. Page
*Assistant Examiner*—William B. Benston, Jr.

[57] ABSTRACT

The described therapeutic compositions with controlled release of medicaments comprise a medicament loaded onto particles of a crosslinked non-ionic polymer insoluble but swellable in water, using either swelling with solutions of the medicament or high-energy co-grinding methods. The medicament-loaded particles are coated with a polymers film able to control medicament release, to obtain a prolonged release of the medicament (even exceeding 24 hours) while maintaining high bioavailability.

10 Claims, No Drawings

THERAPEUTIC COMPOSITIONS WITH CONTROLLED RELEASE OF MEDICAMENTS SUPPORTED ON CROSSLINKED POLYMERS AND COATED WITH POLYMER FILMS, AND THEIR PREPARATION PROCESS

This invention relates to therapeutic compositions with controlled release of medicaments in which particles of non-ionic polymer which is insoluble but swellable in water are loaded with the medicament and coated with a polymer film, and to their preparation process.

STATE OF THE ART

Orally administered medicaments are often poorly absorbed, with consequent very low hematic levels. This problem is accentuated when prolonged release over twelve or even twentyfour hours is required. In this respect, with known pharmaceutical controlled release forms, poorly soluble medicaments normally give rise to hematic levels which in many cases are not even therapeutically valid.

Patent AU-A-8,770,043 describes dispersions or solutions of dihydropyridine derivatives (water-insoluble) in semisolid or liquid non-ionic surfactants. These dispersions result in improved bioavailability. The controlled release is obtained by inserting the dispersions into gelling matrices based on hydrophilic polymers such as hydroxypropylmethylcellulose.

Patent GB-A-2,159,714 describes steroid medicaments with a water solubility of less than one part in 5000 by weight, which are sprayed onto inert cores in the form of suspensions in solutions of water-soluble polymer binders. Successive polymer films of controlled release type are then applied to these cores loaded with the medicament. The improvement in absorption is obtained by micronizing the medicament particles and introducing surface-active wetting agents into the suspension to be sprayed.

Patents DE-A-2,643,004, DE-A-3,320,583 and EP-A-78,430 describe the loading of poorly soluble medicaments onto crosslinked polyvinylpyrrolidone by a method comprising swelling in solvent.

Patent GB-A-2,153,676 describes the loading of the medicament onto crosslinked polyvinylpyrrolidone by a process involving heating the medicament and crosslinked polymer mixture. Patent GB-A-2,153,678 attains the same result by a process involving co-grinding the mixture of medicament and crosslinked polymer in a high-energy mill.

The present applicant (see Italian patent applications IT 22336 A/88 and IT 22770 A/88) has proposed a further two methods for activating poorly soluble medicaments on crosslinked hydrophilic polymers which are insoluble but swellable in water.

All the described patents enable systems comprising medicaments supported on hydrophilic crosslinked polymers to be obtained having a very high solubility or dissolution rate but a very short medicament release time.

Patent SA-A-870,738 (corresponding to EP-A-232,155) describes a system in which the crosslinked polyvinylpyrrolidone is loaded with a solution of the medicament and linear polyvinylpyrrolidone, the loaded product then being mixed with a gelling polymer. The mixture can be granulated or pressed after adding any other excipients.

Patent BE-A-729,827 describes systems consisting of particles or granules of ion exchange resins of size between 0.1 and 1 mm loaded with ionic medicaments and coated with impermeable polymers by coating in a pan.

U.S. Pat. No. 4,221,778 and EP-A-171,528 describe particles of ion exchange resin loaded with ionic medicaments which are pretreated with substances such as polyethyleneglycols or glycerin before coating with polymer films in a fluidized bed.

Patent EP-A-294,103 describes a method in which the ion exchange resins are coated by dispersing the polymer particles (between 5 and 1000 nm) in solutions of the coating polymer, followed by phase separation or spray drying.

Finally, U.S. Pat. No. 4,795,644 describes ion exchange resin particles on which a polymer film containing water-soluble substances such as alkaline metal salts or sugars able to form pores is deposited. It is apparent that in the aforegoing systems the achievement of controlled release is based on the synergic effect between the action of the polymer membrane deposited on the polymer microparticles and the ionic interaction between the resin and the medicament.

DETAILED DESCRIPTION OF THE INVENTION

In contrast to that reported in the aforesaid state of the art, it has been unexpectedly found that the release of medicaments loaded onto particles of non-ionic polymer which is insoluble but swellable in water can be prolonged even for many hours if said medicament-loaded particles are coated with linear polymer delay films.

The present invention therefore provides systems for the controlled release of medicaments supported on crosslinked polymers and coated with polymer films, their preparation process and the pharmaceutical compositions which contain them.

The process for preparing the systems of the present invention consists essentially of the following steps:
1) loading the particles of water-insoluble but water-swellable polymer with the required medicament either by swelling with solutions of the medicament followed by drying, or by high-energy co-grinding;
2) suspending such loaded polymer particles, of between 1 and 200 $\mu$m, in a current of air in a fluidized bed apparatus, spraying them with a solution of the coating polymer, and then drying them in the same apparatus or by another method;
3) size-enlarging the medicament-loaded polymer particles by wet or dry granulation to a homogeneous size of between 100 and 1000 $\mu$m and then coating them as described under point 2.

The size of the coated polymer particles is between the limits of 10–1500 $\mu$m and preferably 100–1000 $\mu$m.

The medicament release system obtained in this manner has a medicament release time which can be adjusted at will from a few hours to 24–48 hours. The medicament loaded onto the polymer particles is in a thermodynamically active state, i.e. amorphous or as extremely small crystals (nanocrystals).

The process according to the invention is implemented in two stages as follows:

1st Stage

The medicament is loaded onto the particles of crosslinked polymer insoluble but swellable in water (or onto a mixture of two or more such polymers) by any known method, such as:

1a) dissolving the medicament in a suitable solvent and spraying a certain volume of the solution onto a given quantity of polymer with the weight ratio of solution to polymer chosen on the basis of the polymer swelling capacity and the medicament concentration in the solution. The spraying can be carried out in any apparatus used for the purpose, such as a continuously stirred reactor, a rotary evaporator under continuous rotation, a mortar by light mixing with a pestle, or a fluidized bed with the polymer kept suspended in an air stream.

The product obtained is then dried in the above apparatus or in other suitable apparatus.

1b) the medicament is dissolved in a suitable solvent and a quantity of a crosslinked polymer insoluble but swellable in water (or a mixture of two or more such polymers) is suspended in an excess of the solution obtained. The suspension is kept stirring until the polymer particles have swollen. The suspension is then filtered or separated by other suitable means, and the product recovered and dried.

1c) the medicament in powder form and the crosslinked polymer insoluble but swellable in water (or a mixture of two or more such polymers), also in powder form, are homogeneously mixed together and then co-ground in a suitable apparatus such as a ball mill, a high-energy vibration mill, an air jet mill etc.

1d) the medicament in powder form and the crosslinked polymer insoluble but swellable in water (or two or more such polymers), also in powder form, are homogeneously mixed together and then co-ground in a suitable apparatus in which the grinding chamber is saturated with solvent vapour or is subjected to a stream of solvent vapour, the solvent being chosen from those able to swell the polymer. The co-grinding is carried out for example in a ball mill, a high-energy vibration mill or a hammer mill, in which the grinding chamber is connected via a valve and pipe to a solvent reservoir.

1e) the medicament in powder form and the crosslinked polymer insoluble but swellable in water, also in powder form, are mixed together homogeneously and then co-heated to the medicament melting point in an apparatus such as an oven, rotary evaporator, reaction vessel, oil bath etc, until the medicament has melted and has been absorbed by the polymer.

The weight ratio of the medicament to said polymer or polymer mixture is in all cases between 0.1 and 1000 parts by weight of medicament per 100 parts by weight of polymer, and preferably between 10 and 100 parts by weight of medicament per 100 parts by weight of polymer.

2nd Stage

When the polymer has been loaded with the active principle, the powder is directly coated with polymer film. Alternatively the polymer film coating can be applied not directly to the medicament-loaded polymer powder but to granules (or pellets) obtained by a size enlargement process carried out on either the starting powder alone or on a mixture of said powder with suitable excipients.

Non-limiting examples of such size enlargement processes are:

dry granulation, based on pressing the loaded polymer powder or its mixture with suitable excipients, followed by crumbling and screening to the desired size;

wet granulation, based on wetting the loaded polymer powder or its mixture with suitable excipients with an aqueous or solvent solution of binders such as sugars, linear polymers etc. in an arm, sigma or other mixer, then wet-screening the paste, drying the resultant aggregates in a forced-air static dryer or in suspension in a fluidized air bed, then crumbling and screening to the desired size;

rapid wet granulation, based on a process of wetting, kneading and sizing the aggregates in apparatus with high speed homogenization systems, then drying and screening;

wet granulation as heretofore described, followed by extrusion and spherodization to improve the morphology of the granules to be coated, then drying and screening.

When the medicament-loaded polymer powder or its granulate has been obtained, it is coated by suspending a weighed quantity of the powder or granulate in a hot air stream within the drum of a fluidized bed apparatus equipped with a Worster insert and a binary nozzle. The air flow is such as to maintain a continuous change of suspended powder in the region in which the solution or suspension of coating polymer is sprayed. The polymer dispersion (or solution) is fed with a peristaltic pump. The quantity of filming agent sprayed per unit time and the total quantity, the atomization, pressure, the nozzle size, the temperature and the air volume used in executing a cycle depend on the quantity, the dimensions of the product to be coated and the extent of the controlled release to be obtained. On termination of spraying, the product is dried directly in the fluidized bed or in a forced-air oven. If necessary, an anti-adhesion agent can be added to the product to ensure separation of the film-coated particles.

Examples of water-insoluble but water-swellable crosslinked polymers which can be used are:

crosslinked polyvinylpyrrolidone (abbreviated to crospovidone), as described in National Formulary, Supplement 3, page 368;

crosslinked sodium carboxymethylcellulose, as described in National Formulary, Supplement 3, page 367;

crosslinked $\beta$-cyclodextrin polymer, as described in patent WO 83/00809 and by Fenyvest et al. in Pharmazie 39, 473, 1984;

crosslinked dextran, etc. Of particular interest is the use of crosslinked $\beta$-cyclodextrin polymer, which up to now has been used only as a disintegrator for solid pharmaceutical compositions and not as a support for medicaments, and the use of crospovidone.

It should however be noted that according to the present invention any polymer having the following characteristics can be used:

a hydrophilic polymer lattice which results in considerable swellability in water water-insolubility by virtue of the nature of the polymer lattice. Non-limiting examples of linear polymers which can be deposited as coating films on the particles of crosslinked polymer previously loaded with the medicament are:

cellulose and derivatives soluble or insoluble in aqueous solutions, such as: ethylcellulose, methylcellulose, hydroxypropylcellulose, hydroxypropylmethylcellulose, cellulose acetate, cellulose acetobutyrate, cellulose acetotrimellitate, cellulose acetophthalate etc.

acrylic and methacrylic polymers and their copolymers soluble or insoluble in aqueous solutions such as: methacrylic acid-methylmethacrylate copolymer, ethylacrylate-methylmethacrylate copolymer, ethylacrylate-methylmethacrylate and trimethylammonium ethylmethacrylate chloride copolymer etc.

linear polyvinylpyrrolidone of differing molecular weight, vinylpyrrolidone-vinyl acetate copolymer etc.

polyanhydrides such as vinylether-maleic anhydride copolymer polyvinylalcohol.

It should however be noted that according to the present invention any polymer having the following characteristics can be used:

insolubility at all pH values solubility only at determined pH values (e.g. 4.5, 5.5, 6.0, 7.0)

solubility at all pH values.

The aforesaid polymers can be used either alone or in mixture, with the addition of suitable plasticizers such as glycerin, polyethyleneglycols, citric acid esters, glycerin esters, phthalic acid lo esters etc.; of anti-adhesion substances such as talc, silica, magnesium stearate etc.; or of porogenic substances such as microcrystalline lactose, calcium carbonate, calcium phosphate, saccharose, sodium chloride, potassium chloride etc.

There are no particular limitations to the medicaments which can be used according to the present invention, and in fact either water-soluble medicament or medicaments poorly soluble in water can be used. Non-limiting examples of medicaments poorly soluble in water which can be used according to the present invention are: griseofulvin, indomethacin, diacerein, megestrol acetate, estradiol, progesterone, medroxyprogesterone acetate, nifedipine, nicergoline, paracetamol, clonidine, etoposide, lorazepam, temazepam, digoxin, glibenclamide ketoprofen, indobufen, ibuprofen, diclofenac, naproxene, acemethacine etc.

In the case of water-soluble medicaments, the main advantage of the present invention is that their incorporation into the spherical particles of the water-insoluble crosslinked polymer facilitates the subsequent coating with polymer film. In this respect, in many cases the original morphology of said medicaments is very irregular (needles, very thin flakes etc.) and makes homogeneous and continuous coating of the particles over their entire surface difficult, with consequent poor control of the medicament release. In the particular case of insoluble medicaments in the form of weak acid salts of strong bases one advantage of the present invention is that their incorporation into the insoluble crosslinked polymer provides them with greater protection against the surrounding ph-variable environment in the different segments of the intestinal tract, this variable pH being able to influence the degree of ionization of the medicament and consequently its permeation characteristics. In order to control this ionization, the insoluble crosslinked polymer can also be loaded with agents able to suitably change the pH within the crosslinked polymer itself.

Non-limiting examples of water-soluble medicaments which can be used according to the present invention are: diltiazem hydrochloride, nicardipine hydrochloride, sodium chloride, captopril, enalapril, theophylline, ranitidine, verapanil hydrochloride, naproxene sodium salt, diclofenac sodium salt, propanolol, atenolol etc.

EXAMPLE 1

600 g of CROSPOVIDONE (Kollidon CL, BASF) were loaded with 120 g of griseofulvin dissolved in 1.2 liters of methylenechloride in a chamber of a sigma mixer under continuous mixing. The thus swollen powder was dried in the same chamber at ambient temperature, at a residual pressure of 450°-500 mbar; drying was completed in an oven under vacuum for 1 hour at 30° C.

700 g of the powdered polymer loaded with griseofulvin in the aforesaid manner were mixed with 35 g of talc F.U. and 3.5 g of Aerosil 200 and were suspended in a 6" Worster column of a GPCG1 fluidised bed plant and coated with 700 g of colloidal suspension of acrylic polymer EUDRAGIT RS 30D (ROEHM PHARMA) with added talc F.U., triethylcitrate plasticizer and Tween 80 surfactant under the following operating conditions: atomization pressure 1-1.5 bar, feed rate of coating suspension 8-10 g/min, inlet air temperature 50° C., product temperature 22°-25° C.

On termination of spraying, drying was carried out at the same inlet air temperature. The thus coated powder had the following percentage composition:

| | |
|---|---|
| Griseofulvin | 12.91 |
| PVP CL | 64.28 |
| EUDRAGIT RS | 8.11 |
| TALC F.U. | 12.68 |
| CITROFLEX 2 | 1.63 |
| TWEEN 80 | 0.01 |
| SiO$_2$ | 0.38 |
| | 100.00 |

EXAMPLE 2

120 g of griseofulvin dissolved in 1.2 liters of methylene chloride were loaded onto 600 g of crospovidone (kollidon CL, BASF) kept under continuous mixing in a suitably sized sigma mixer. The thus swollen powder was dried in the same apparatus under vacuum (450-500 mbar of residual pressure) at ambient temperature. Drying was complete in an oven under vacuum for 1 hour at 30° C.

700 g of the powdered polymer loaded with griseofulvin in the aforesaid manner were mixed with 35 g of talc F.U. and 3.5 g of Aerosil 200 and were suspended in a 6" Worster column of a GPCG1 fluidised bed plant (GLATT, West Germany) and coated with 1050 g of colloidal suspension of acrylic polymer Eudragit RS 30D (ROEHM PHARMA) with added talc F.U. (anti-adhesion agent), triethylcitrate (plasticizer) and Tween 80 under the following operating conditions: atomization pressure 1-1.5 bar, feed rate of coating suspension 8-10 g/min, air volume during process 2-3 m$^3$/min, inlet air temperature 50° C., product temperature 22°-25° C.

On termination of spraying, drying was carried out at the same inlet air temperature and volume. The thus coated powder had the following percentage composition:

| | |
|---|---|
| Griseofulvin | 11.77 |
| PVP CL | 58.67 |
| EUDRAGIT RS | 11.33 |
| TALC F.U. | 15.60 |

| | |
|---|---|
| CITROFLEX 2 | 2.26 |
| TWEEN 80 | 0.02 |
| SiO₂ | 0.35 |
| | 100.00 |

EXAMPLE 3

250 g of diacerein were activated by high-energy grinding with 250 g of povidone (Kollidon CL-M, BASF). 500 g of a mixture of excipients (30% lactose, 40% microcrystalline cellulose and 30% corn starch) were added to the 500 g of co-ground product and the resultant mixture was wet-granulated using a 5% solution of hydroxypropylcellulose in water as binder. The mixture was wet-screened and dried in a fluidized bed (GPCG1 Glatt, West Germany) under the following operating conditions: inlet air temperature 55° C., inlet air volume 1-1.5 m³/min. The product was then dry-screened in an oscillating granulator. 2 g of granulate prepared as described were suspended in a 4" Worster column of a OPCGL fluidised bed plant (Glatt, West Germany) and coated with 160 g of colloidal suspension of acrylic polymer Eudragit NE 30D (ROEHM PHARMA) with added talc F.U. (anti-adhesion agent), under the following operating conditions: atomization pressure 1-1.5 bar, feed rate of coating suspension 2-3 g/min, inlet air temperature 30°-40° C., product temperature 25°-30° C., air volume during process 1.5-2 m³/min. On termination of spraying, drying was carried out at the same inlet air temperature and volume. The thus coated granulate had the following percentage composition:

| | |
|---|---|
| Diacerein | 21.45 |
| PVP CL | 21.45 |
| EUDRAGIT NE | 8.80 |
| LACTOSE | 12.83 |
| MICROCRYSTALLINE CELLULOSE | 17.14 |
| HYOROXYPROPYLCELLULOSE | 2.20 |
| CORN STARCH | 12.83 |
| TALC F.U. | 3.30 |
| | 100.00 |

EXAMPLE 4

500 g of granulate obtained as described in Example 3 (particle size distribution 300-800 μm) were suspended in a 6" Worster column of a GPCG1 fluidised bed plant (Glatt, West Germany) and coated with 560 g of colloidal suspension of acrylic polymer Eudragit RS 30D (ROEHM PHARMA) with added talc F.U. (anti-adhesion agent), triethylcitrate (plasticizer) and Tween 80 under the following operating conditions: atomization pressure 1.5 bar, feed rate of coating suspension 10-12 g/min, air volume during process 2-3 m³/min, inlet air temperature 50°-60° C., product temperature 30°-35° C. On termination of spraying, drying was carried out at the same inlet air temperature and volume. The thus coated granulate had the following percentage composition:

| | |
|---|---|
| Diacerein | 19.68 |
| PVP CL | 19.68 |
| EUDRAGIT RS | 12.09 |
| LACTOSE | 11.78 |
| MICROCRYSTALLINE CELLULOSE | 15.72 |
| HYDROXYPROPYLCELLULOSE | 2.01 |
| CORN STARCH | 11.78 |
| TALC F.U. | 4.83 |
| TRIETHYLCITRATE | 2.41 |
| TWEEN 80 | 0.02 |
| | 100.00 |

EXAMPLE 5

200 g of granulate prepared as described in Example 3 were suspended in a 4" Worster column of a GPCG1 fluidised bed plant (Glatt, West Germany) and coated with 125 g of colloidal suspension of Eudragit RS 30D and Eudragit RL 30D acrylic polymer with added talc F.U. (anti-adhesion agent), triethylcitrate (plasticizer) and Tween 80 under the following operating conditions: atomization pressure 1-1.5 bar, feed rate of coating suspension 2.5-5 g/min, inlet air temperature 55°-6° C., product temperature 30°-32° C., air volume during process 1-1.5 m³/min. On termination of spraying, drying was carried out at the same inlet air temperature and volume. The thus coated granulate had the following percentage composition:

| | |
|---|---|
| Diacerein | 21.78 |
| PVP CL | 21.78 |
| EUDRAGIT RS | 3.35 |
| EUDRAGIT RL | 3.35 |
| LACTOSE | 13.04 |
| CELLULOSE | 17.41 |
| HYDROXYPROPYLCELLULOSE | 2.23 |
| CORN STARCH | 13.04 |
| TALC F.U. | 2.67 |
| TRIETHYLCITRATE | 1.34 |
| TWEEN 80 | 0.01 |
| | 100.00 |

EXAMPLE 6

200 g of granulate prepared as described in Example 3 were suspended in a 4" Worster column of a GPCG1 fluidised bed plant (Glatt, West Germany) and coated with 1000 g of a 10% solution of Eudragit L100 acrylic polymer in a mixture composed of 6 parts of ethanol and 4 parts of deionized water with added talc F.U. (anti-adhesion agent) and n-dibutylphthalate (plasticizer) under the following operating conditions: atomization pressure 1 bar, feed rate of coating suspension 2-6 g/min, inlet air temperature 40°-45° C., product temperature 30°-35° C., air volume during process 1.5-2 m³/min. On termination of spraying, drying was carried out at the same inlet air temperature and volume. The thus coated granulate had the following percentage composition:

| | |
|---|---|
| Diacerein | 14.78 |
| PVP CL | 14.78 |
| EUDRAGIT L | 30.30 |
| LACTOSE | 8.84 |
| CELLULOSE | 11.82 |
| HYDROXYPROPYLCELLULOSE | 1.52 |
| CORN STARCH | 8.84 |
| TALC F.U. | 3.04 |
| N-DIBUTYLPHTHALATE | 6.08 |
| | 100.00 |

EXAMPLE 7

45 g of nifedipine dissolved in 450 cc of methylene chloride were loaded onto 225 g of Povidone (Kollidon CL-M, BASF) kept under constant stirring in a sigma mixer. After homogenization of the pasty mass the swelling solvent was extracted by a vacuum pump at a residual pressure of 450-500 mbar. After evaporation and recovery of the methylene chloride the loaded product was collected and drying completed in a vacuum oven (1 hour at 30° C.)

The 270 g of prepared product were returned to the mixing chamber of the sigma mixer and exposed to methylene chloride vapour for 24 hours. This operation was followed by drying in an oven, screening and homogenization by mixing the product. Colloidal silica (Aerosil 200, Degussa) was added to the final loaded product, which was then divided into flat tablets of 15 mm diameter weighing 500 mg and having a hardness of 7-10 Kp. These tablets were then reduced to granules with an oscillating granulator (or knife mill). The 425-1200 μm granulate fraction was removed by screening.

200 g of the granulate prepared as aforedescribed were suspended in a 4" Worster column of a GPCG1 fluidised bed plant (Glatt, West Germany) and coated with 1330 g of a solution of Eudragit S100 acrylic polymer (ROEHM PHARMA)in ethanol/H$_2$O (80/20) with added talc F.U. (anti-adhesion agent) and n-dibutylphthalate (plasticizer) under the following operating conditions: atomization pressure 1-1.5 bar, feed rate of coating suspension 3.5-5 g/min, inlet air temperature 38°-4° C., product temperature 30°-32° C., air volume during process 1.5-2.5 m$^3$/min. On termination of spraying, drying was carried out at the same inlet air temperature and volume. The thus coated granulate had the following percentage composition:

| Nifedipine | 10 |
|---|---|
| PVP CL | 50 |
| COLLOIDAL SILICA | 0.61 |
| EUDRAGIT S | 30.3 |
| N-DIBUTYLPHTHALATE | 3.03 |
| TALC F.U. | 6.06 |
| | 100.00 |

EXAMPLE 8

200 g of granulate prepared as described in Example 7 were suspended in a 4" Worster column of a GPCG1 fluidised bed plant (Glatt, West Germany) and coated with 833 g of colloidal suspension of Eudragit L30D acrylic polymer (ROEHM PHARMA) with added talc F.U. (anti-adhesion agent), n-dibutylphthalate (plasticizer) and Tween 80 under the following operating conditions: atomization pressure 1-1.5 bar, feed rate of coating suspension 3-5 g/min, inlet air temperature 48°-52° C., product temperature 30°-34° C., air volume during process 1.5-2.5 m$^3$/min. On termination of spraying, drying was carried out at the same inlet air temperature and volume. The thus coated granulate had the following percentage composition:

| Nifedipine | 10 |
|---|---|
| PVP CL | 50 |
| EUDRAGIT L30D | 30.3 |
| COLLOIDAL SILICA | 0.61 |
| N-DIBUTYLPHTHALATE | 3.0 |
| TALC F.U. | 6.06 |
| TWEEN 80 | 0.03 |
| | 100.00 |

EXAMPLE 9

200 g of granulate prepared as described in Example 7 were suspended in a 4" Worster column of a GPCG1 fluidised bed plant (Glatt, West Germany) and coated with 525 g of solution of Povidone (Kollidon 25, BASF) in ethanol with added talc F.U. (an-ti-adhesion agent) and glycerin (plasticizer) under the following operating conditions: spraying pressure 1 bar, feed rate of coating suspension 4.5-6 g/min, inlet air temperature 30°-34° C., product temperature 28°-30° C., air volume during process 1.5-2 m$^3$/min. On termination of spraying, drying was carried out at the same inlet air temperature and volume. 215 g of this coated granulate were suspended in a 4" Worster column of a GPCG1 fluidised bed plant (Glatt, West Germany) and coated with 285 g of colloidal suspension of ethylcellulose (Aquacoat ECD-30 FMC) with added talc F.U. (anti-adhesion agent), n-triethylcitrate (plasticizer) under the following operating conditions: atomization pressure 1-1.5 bar, feed rate of coating suspension 3.5-5.5 g/min, inlet air temperature 50°-55° C., product temperature 30°-35° C., air volume during process 1.5-2 m$^3$/min. On termination of spraying, drying was carried out at the same inlet air temperature and volume. Percentage composition of final coated product:

| Nifedipine | 12.35 |
|---|---|
| PVP CL | 61.8 |
| Colloidal silica | 0.75 |
| PVP K25 | 5.14 |
| Glycerin | 0.48 |
| ETHYLCELLULOSE | 14.98 |
| TRIETHYLCITRATE | 4.5 |
| | 100.00 |

EXAMPLE 10

215 g of granulate coated as described in the first part of Example 9 were suspended in a 4" Worster column of a GPCG1 fluidised bed plant (Glatt, West Germany) and coated with 285 g of colloidal suspension of ethylcellulose (Aquacoat ECD-30 FMC) with added hydroxypropyl methylcellulose (Methocel E5, Dow Chemical) and triethylcitrate (plasticizer) under the following operating conditions: atomization pressure 1-1.5 bar, feed rate of coating suspension 4-8 g/min, inlet air temperature 50°-55° C., product temperature 32°-35° C., air volume during process 1.5-2 m$^3$/min. On termination of spraying, drying was carried out at the same inlet air temperature and volume. The coated product was then discharged and 1% of powdered talc F.U. added, after which it was placed in an oven at a temperature of 60° C. for 2 hours. The thus coated granulate had the following percentage composition:

| Nifedipine | 12.35 |
|---|---|
| PVP CL | 61.75 |
| Colloidal silica | 0.75 |
| PVP K25 | 5.14 |
| GLYCERIN | 0.71 |
| HYDROXYPROPYLMETHYLCELLULOSE | 3.7 |

| | |
|---|---|
| ETHYLCELLULOSE | 11.1 |
| TRIEIHYLCITRATE | 4.5 |
| | 100.00 |

EXAMPLE 11

45 g of ketoprofen dissolved in 450 cc of methylene chloride were loaded onto 225 g of crosslinked β-cyclodextrin (Ciclolab-Chinoin, Budapest) kept under constant stirring in a sigma mixer. After homogenization of the pasty mass the swelling solvent was extracted by a vacuum pump at a residual pressure of 450-500 mbar. After evaporation and recovery of the methylene chloride the loaded product was collected and drying completed in a vacuum oven (1 hour at 30° C.) The 270 g of prepared product were then screened and homogenized by mixing. Colloidal silica (Aerosil 200, Degussa) and magnesium stearate were added to the final loaded product, which was then divided into flat tablets of 15 mm diameter weighing 500 mg. These tablets were then reduced to granules with a knife mill (or oscillating granulator). The 425-1000 μm granulate fraction as removed by screening.

200 g of the granulate prepared as described above were suspended in a 4" Worster column of a GPCG1 fluidised bed plant (Glatt, West Germany) and coated with 525 g of solution of Povidone (Kollidon 25, BASF) in ethanol with added talc F.U. (anti-adhesion agent) and glycerin (plasticizer) under the following operating conditions: spraying pressure 1 bar, feed rate of coating suspension 4.5-6 g/min, inlet air temperature 30°-34° C., product temperature 28°-30° C., air volume during process 1.5-2.5 m³/min. On termination of spraying, drying was carried out at the same inlet air temperature and volume.

215 g of this coated granulate were suspended in a 4" Worster column of a GPCG1 fluidised bed plant (Glatt, West Germany) and coated with 285 g of colloidal suspension of ethylcellulose (Aquacoat ECD-30 FMC) with added triethylcitrate (plasticizer) under the following operating conditions: spraying pressure 1-1.5 bar, feed rate of coating suspension 3.5-5.5 g/min, inlet air temperature 50°-55° C., product temperature 30°-35° C., air volume during process 1.5-2 m³/min. On termination of spraying, drying was carried out at the same inlet air temperature and volume. Percentage composition of final coated product:

| | |
|---|---|
| Ketoprofen | 12.35 |
| Crosslinked β-cyclodextrin | 61.8 |
| Colloidal silica | 0.37 |
| Magnesium stearate | 0.37 |
| PVP K25 | 5.15 |
| Glycerin | 0.48 |
| Ethylcellulose | 14.98 |
| | 4.51 |
| | 100.00 |

EXAMPLE 12

293 g of diltiazem hydrochloride are activated by high-energy co-grinding with 1479 of PVP CL using a ball mill.

The duration of the grinding cycle is 2 hours at the maximum speed of the mill.

424 g of 2:1 co-ground diltiazem/PVP CL are granulated in a fluidized bed (Glatt GPCG1 W.G.) using a binding polymer granulating dispersion. 208 g of the obtained granulate are formulated as follows:

| | |
|---|---|
| Granulated diltiazem | 208 g |
| Magnesium stearate | 4.5 g |
| Micronized talc | 1 g |
| Avicel PH 102 | 38 g |
| | 251.5 g | and the mixture is pressed using an automatic rotary press. The tablets obtained are granulated in a VIANI oscillating granulator through a screen of 1.3 mm mesh.

225 g of granulate prepared as described are suspended in a 4" Worster column of a GPCG1 fluidised bed plant (Glatt, W.G.) and coated to the extent of 10% with 301.6 g of an alcoholic solution of Eudragit RS PM acrylic polymer (Röhm Pharma) using the following formulation for the coating:

| | |
|---|---|
| Eudragit RS PM | 22.5 g |
| Micronized talc | 4.48 g |
| Citroflex 2 | 4.48 g |
| 96% ethanol | 270.16 g |

This first coating is applied to the extent of 10% by weight of the granulate, under the following operating conditions:

| | |
|---|---|
| atomization pressure | 1 bar |
| feed rate of coating suspension | 5.6 g/min |
| air inlet temperature | 30° C. |
| product temperature | 25° C. |

230 g of the granulate previously coated with 10% of Eudragit RS PM are suspended in the previously used 4" Worster column and coated with 182 g of a Eudragit NE 30D polymer suspension.

| Film coating composition: | |
|---|---|
| Eudragit NE 30D | 76.64 g (23 dry) |
| Micronized talc | 7 g |
| Water | 98.37 g |

The total coating is therefore 20%. On completion of the coating procedure, rapid drying is effected under the same air conditions. The thus coated granulate had the following percentage composition:

| | |
|---|---|
| Diltiazem HCl | 38.85 |
| PVP CL | 19.49 |
| Eudragit NE 30D | 14.68 |
| Eudragit RS PM | 7.80 |
| Magnesium stearate | 1.39 |
| Micronized talc | 4.55 |
| Avicel PH 102 | 11.7 |
| Citroflex 2 | 1.54 |
| TOTAL | 100.00 |

For purposes of comparison the following compositions were prepared by simply loading the medicament onto the swellable hydrophilic polymer but without coating with the polymer film.

EXAMPLE A 600 g of crospovidone (Kollidon CL, BASF) were loaded with 120 g of griseofulvin dissolved in 1.2 liters of methylene chloride in a chamber of a sigma mixer under continuous mixing. The thus swollen powder is dried in the same chamber at ambient temperature under a residual pressure of 450-500 mbar. Drying is completed in a vacuum oven for 1 hour at 30° C.

| % composition: | |
|---|---|
| Griseofulvin | 16.6 |
| PVP CL | 83.4 |
| | 100.00 |

EXAMPLE B 250 g of diacerein were activated by high-energy grinding with 250 g of crospovidone (Kollidon CL-M, BASF). 500 g of a mixture of excipients (30% lactose, 40% microcrystalline cellulose, 30% corn starch) were then added to the 500 g of co-ground product and the resultant mixture wet-granulated using a 5% hydroxypropyl cellulose solution in water as binder. The mixture was wet-screened and dried in a fluidized bed (GPCG1 Glatt, West Germany) under the following operating conditions: air inlet temperature 55° C., air inlet volume 1-1.5 m³/min. The product was then dry-screened in an oscillating granulator.

| % composition: | |
|---|---|
| Diacerein | 24.4 |
| PVP CL | 24.4 |
| Cellulose | 19.5 |
| Corn starch | 14.6 |
| Lactose | 14.6 |
| Hydroxypropyl cellulose | 2.5 |
| | 100.00 |

EXAMPLE C 45 g of nifedipine dissolved in 450 cc of methylene chloride were loaded onto 225 g of crospovidone (Kollidon CL-M, BASF) kept under constant stirring in a sigma mixer. After homogenization of the pasty mass the swelling solvent was extracted by a vacuum pump at a residual pressure of 450-500 mbar. After evaporation and recovery of the methylene chloride the loaded product was collected and drying completed in a vacuum oven (1 hour at 30° C.)

The 270 g of prepared product were returned to the mixing chamber of the sigma mixer and exposed to methylene chloride vapour for 24 hours. This operation was followed by drying in an oven, screening and homogenization by mixing the product. Colloidal silica (Aerosil 200, Degussa) was added to the final loaded product, which was then divided into flat tablets of 15 mm diameter weighing 500 mg and having a hardness of 7-10 Kp. These tablets were then reduced to granules with an oscillating granulator (or knife mill). The 425-1200 μm granulate fraction was removed by screening.

| % composition: | |
|---|---|
| Nifedipine | 16.6 |
| PVP CL | 82.9 |
| Colloidal silica | 0.5 |
| | 100.0 |

EXAMPLE D 293 g of diltiazem hydrochloride are activated by high-energy co-grinding with 1479 of PVP Cl using a ball mill. The duration of the grinding cycle is 2 hours at the maximum speed of the mill.

| % composition: | |
|---|---|
| Diltiazem HCl | 66.6 |
| PVP CL | 33.4 |
| | 100.0 |

Determination of Dissolution Rate

The dissolution data for the productions prepared by the process of this invention (Examples 1 to 12) are given in Tables 1-5. For comparison, each table also shows the dissolution rate data for the products prepared by simple loading onto the swellable hydrophilic polymer without subsequent coating with a polymer film (Examples A, B, C and D)

The method used for all the studied medicaments was the U.S.P. XXI No. 2 method using the SOTAX apparatus at 37° C. and a Beckman Du 65 spectrophotometer.

For the products containing griseofulvin 900 ml of pH 7.5 buffer were used with stirring at 150 r.p.m. The spectrophotometric reading of the suitably diluted samples was performed at $\alpha = 294$ nm.

For the products containing diacerein 900 ml of pH 5.5 buffer were used with stirring at 100 r.p.m. The spectrophotometric reading of the suitably diluted samples was performed at $\alpha = 255$ nm.

For the products containing nifedipine 900 ml of pH 7.5, pH 4.6 and pH 5.5 buffer with and without Tween 80 as surfactant were used with stirring at 150 r.p.m. The spectrophotometric reading of the suitably diluted samples was performed at $\alpha = 235$ nm.

For the products containing diltiazem 900 ml of pH 7.5, pH 5.5 and pH 1.2 buffer were used with stirring at 100 r.p.m. The spectrophotometric reading of the suitably diluted sampled was performed at $\alpha = 233$ nm.

As can be seen from the data of Tables 1-5, for all the medicaments and all the coating polymers used, in every case there was a clearly more delayed and controlled dissolution rate for the products prepared by the process of this invention than for the analogous products prepared exclusively by loading onto the swellable hydrophilic polymer.

Table 4 also shows the release at different pH values for nifedipine from particles of crosslinked polyvinylpyrrolidone coated with acrylic polymer of ph-dependent solubility. It is evidently possible with the product of the present invention to obtain release rates which differ greatly with pH.

TABLE 1

Dissolution rate of products containing griseofulvin loaded onto crospovidone and coated with acrylic polymer:

| | % GRISEOFULVIN RELEASED | | |
|---|---|---|---|
| TIME | Comparison preparation (EXAMPLE A) | Invention preparation (EXAMPLE 1) | Invention preparation (EXAMPLE 2) |
| 15 min | 47.6% | 16.2% | 22.2% |
| 30 min | 65.7% | 26.3% | 30.3% |
| 60 min | 83.8% | 38.9% | 41.5% |
| 120 min | | 55.9% | 54.2% |
| 180 min | | 69.3% | 68.5% |

TABLE 1-continued

Dissolution rate of products containing griseofulvin loaded onto crospovidone and coated with acrylic polymer:

| | % GRISEOFULVIN RELEASED | | |
|---|---|---|---|
| TIME | Comparison preparation (EXAMPLE A) | Invention preparation (EXAMPLE 1) | Invention preparation (EXAMPLE 2) |
| 240 min | | 76.6% | 74.0% |
| 360 min | | 80.2% | |
| 480 min | | 88.2% | 81.2% |
| 600 min | | 96.0% | 85.6% |
| 720 min | | | 89.9% |

TABLE 2

Dissolution rate of products containing diacerein loaded onto crospovidone and coated with acrylic polymer:

| | % DIACEREIN RELEASED | | | | |
|---|---|---|---|---|---|
| TIME | Comparison preparation (EXAMPLE B) | Invention preparation (EXAMPLE 3) | Invention preparation (EXAMPLE 4) | Invention preparation (EXAMPLE 5) | Invention preparation (EXAMPLE 6) |
| 15 min | 83.4% | 5.4% | 3.3% | 9.9% | 3.5% |
| 30 min | 94.6% | 7.2% | 4.2% | 18.3% | 5.3% |
| 60 min | 100.7% | 12.9% | 4.9% | 31.4% | 12.9% |
| 120 min | | 22.6% | 7.9% | 47.8% | 32.4% |
| 180 min | | 29.1% | 10.8% | 60.6% | 51.0% |
| 240 min | | 36.2% | 12.7% | 64.4% | 66.6% |
| 360 min | | 44.1% | 15.9% | 71.5% | 81.3% |
| 420 min | | 45.5% | 17.0% | 75.2% | 90.4% |
| 480 min | | 48.5% | 19.8% | 79.2% | 93.0% |
| 540 min | | 49.4% | 21.2% | 82.4% | |
| 600 min | | 51.3% | | 83.6% | |
| 720 min | | 58.2% | | | |

TABLE 3

Dissolution rate of products containing nifedipine loaded onto crospovidone and coated with acrylic polymers and cellulose derivatives:

| | % NIFEDIPINE RELEASED | | | | |
|---|---|---|---|---|---|
| | Comparison preparation (EXAMPLE C) | Invention preparation (EXAMPLE 8) | | Invention preparation (EXAMPLE 9) | Invention preparation (EXAMPLE 10) |
| TIME | pH 7.5 | pH 4.6 | pH 7.5 | pH 7.5 + 1% tween 80 | PH 7.5 + 1% tween 80 |
| 15 min | 64.8% | | 80.0% | 12.1% | 34.4% |
| 30 min | 87.5% | 30.0% | 98.9% | 13.0% | 49.4% |
| 60 min | 104.8% | 33.0% | | 13.2% | 54.3% |
| 120 min | | 36.1% | | 15.5% | 58.6% |
| 180 min | | | 105.0% | 16.4% | 61.2% |
| 300 min | | | 41.2% | | 71.0% |
| 360 min | | | | 22.4% | |
| 420 min | | 42.6% | | | 75.1% |

TABLE 4

Influence of pH on dissolution rate of products containing nifedipine loaded onto crospovidone and coated with acrylic polymer of pH-dependent solubility

| | % NIFEDIPINE RELEASED | | |
|---|---|---|---|
| | Comparison preparation | Invention preparation | |
| | (EXAMPLE C) | (EXAMPLE 7) | |
| TIME | pH 7.5 | pH 5.5 | pH 7.5 |
| 15 min | 64.8% | 17.2% | 62.3% |
| 30 min | 87.5% | 29.0% | 64.6% |
| 60 min | 104.8% | 38.2% | 90.5% |
| 120 min | | 38.6% | 108.0% |

TABLE 5

Dissolution rate of products containing diltiazem hydrochloride loaded onto crospovidone and coated with polymers:

| | % DILTIAZEM HCl RELEASED | |
|---|---|---|
| TIME | Comparison preparation (EXAMPLE D) | Invention preparation (EXAMPLE 12) |
| 1 min | 86.9% | — |
| 2 min | 96.0% | — |
| 3 min | 96.8% | — |
| 15 min | | 2.5% |
| 60 min | | 3.2% |
| 120 min | | 10.5% |
| 240 min | | 25.7% |
| 360 min | | 41.4% |
| 480 min | | 61.0% |
| 600 min | | 85.4% |

We claim:

1. Therapeutic compositions with controlled release of medicaments, consisting of particles of a crosslinked, non-ionic polymer insoluble but swellable in water, which are loaded with the medicament and coated with a polymer film.

2. Compositions as claimed in claim 1, wherein the non-ionic polymer insoluble but swellable in water is a mixture of polymers.

3. Compositions as claimed in claim 1, wherein the polymer loaded with the medicament is crosslinked β-cyclodextrin polymer.

4. Compositions as claimed in claim 1, wherein the polymer loaded with the medicament is crospovidone.

5. Compositions as claimed in claim 1, wherein the polymer coating film consists of one or more linear polymers.

6. Compositions as claimed in claim 1, wherein the non-ionic polymer particles have a size of between 1 and 200 $\mu$.

7. Compositions as claimed in claim 1, wherein the non-ionic polymer particles have a size of between 100 and 1000 $\mu$.

8. A process for preparing therapeutic compositions with controlled release of medicaments, comprising:
   loading with medicament particles of a polymer which is insoluble, but swellable in water,
   optionally enlarging the size of said loaded-polymer particles by wet or dry granulation,
   suspending said loaded-polymer particles in an air stream,
   spraying said loaded-polymer particles with a solution of a coating polymer, and
   drying said polymer-coated particles.

9. A process as claimed in claim 8, wherein the weight ratio of medicament to polymer particles is between 0.1 and 1000 parts of medicament per 100 parts of polymer.

10. A process as claimed in claim 8, wherein the ratio is between 10 and 100 parts of medicament per 100 parts of polymer.

* * * * *